(12) United States Patent
Miles et al.

(10) Patent No.: US 6,307,626 B1
(45) Date of Patent: Oct. 23, 2001

(54) DISPERSIVE ATOMIC VAPOR RAMAN FILTER

(75) Inventors: Richard B. Miles, Princeton; Walter R. Lempert, Mercerville; Noah Finkelstein, Princeton, all of NJ (US)

(73) Assignee: Plasma Tec, Inc., Princeton, NJ (US)

( * ) Notice: Subject to any disclaimer, the term of this patent is extended or adjusted under 35 U.S.C. 154(b) by 0 days.

(21) Appl. No.: 09/446,369

(22) PCT Filed: Jun. 18, 1998

(86) PCT No.: PCT/US98/12752

§ 371 Date: Mar. 20, 2000

§ 102(e) Date: Mar. 20, 2000

(87) PCT Pub. No.: WO98/59225

PCT Pub. Date: Dec. 30, 1998

Related U.S. Application Data

(60) Provisional application No. 60/050,320, filed on Jun. 20, 1997.

(51) Int. Cl.[7] .................................. G01J 3/44; G01N 21/65
(52) U.S. Cl. .................................................. 356/301
(58) Field of Search ............................................. 356/301

(56) References Cited

U.S. PATENT DOCUMENTS

| | | | |
|---|---|---|---|
| 2,483,244 | 9/1949 | Stamm | 356/301 |
| 2,940,355 | 6/1960 | Cary | 356/301 |
| 3,909,132 | 9/1975 | Barrett | 356/45 |
| 4,586,819 | 5/1986 | Tochigi et al. | 356/301 |
| 4,684,258 | 8/1987 | Webster | 356/409 |
| 5,217,306 | 6/1993 | Wada | 374/161 |
| 5,261,410 | 11/1993 | Alfano et al. | 128/664 |
| 5,262,644 | 11/1993 | Maguire | 250/339 |
| 5,449,233 | 9/1995 | Sai et al. | 374/161 |
| 5,498,875 | 3/1996 | Obremski et al. | 250/458.1 |
| 5,506,678 | 4/1996 | Carlsen et al. | 356/338 |
| 5,618,108 | 4/1997 | Sai et al. | 374/161 |
| 5,638,172 | 6/1997 | Alsmeyer et al. | 356/301 |
| 5,786,893 | * 7/1998 | Fink et al. | 356/301 |

* cited by examiner

Primary Examiner—F. L. Evans
(74) Attorney, Agent, or Firm—Wolff & Samson

(57) ABSTRACT

A method and apparatus for collecting and analyzing Raman scattered light includes an atomic vapor cell (10) configured to spectrally disperse light by resonant dispersion while simultaneously suppressing Rayleigh scattering and other background scattering through resonant absorption. A light source (1) is used to illuminate a sample (2). The light source (1) is tuned in the vicinity of the absorption feature of some atomic vapor. The resonant dispersion of the vapor is well known to strongly vary in the vicinity of such an absorption feature. If the light source (1) is tuned in the vicinity of the absorption, then the Rayleigh light is strongly attenuated. The Raman light is transmitted through the filter. If the filter is constructed so that the dispersive nature of the atomic vapor in the vicinity of the absorption line bends the light rays as they pass through the atomic vapor cell (10), then the Raman light can be spatially displaced.

29 Claims, 5 Drawing Sheets

DISPERSIVE ATOMIC VAPOR RAMAN FILTER

This application claims benefit of provisional application Ser. No. 60/050,320 filed Jun. 20, 1997.

BACKGROUND OF THE INVENTION

1. Field of the Invention

This invention relates to a method and apparatus for collecting and analyzing Raman scattered light. The apparatus includes an atomic vapor cell configured to spectrally disperse the light by resonant dispersion while simultaneously suppressing the Rayleigh Scattering and other background scattering through resonant absorption.

2. Related Art

Raman spectroscopy has long been a primary tool for molecular diagnostics. The Raman mechanism is based on light scattering from molecules in a sample volume and is usually done using a narrow linewidth laser as a source. When a sample is illuminated, the light that scatters from it echoes the character of the molecules in the sample volume. If the source has a narrow frequency band, then one can distinguish several molecular scattering mechanisms by the spectrum of the light that is collected. Assuming that the illumination frequency is far away from a resonant absorption feature associated with any of the molecules in the sample volume, then there are three primary components of the scattered light. The strongest component is the elastic scattering from the molecules. This light is usually termed Rayleigh Scattering, and it is only very slightly shifted in frequency from the source frequency due to the Doppler effect associated with the translational motion of the molecules. A second component arises from scattering off of the acoustic waves in the medium and is frequency shifted by the Doppler shift associated with the speed of sound. The second component is often call Brillouin Scattering, and it appears most notable in high pressure or low temperature gases where the mean free path of the molecules is small compared to the relevant acoustic wavelength. The third component, Raman scattering, is due to inelastic scattering from the molecules themselves and is associated with the internal modes of molecular energy. Since the internal modes of energy are unique to each molecular species, this type of scattering is exceptionally useful. The presence of specific spectral features indicates the presence of particular molecules in the sample volume, and the strength of the features can be interpreted to give the concentration of those molecules and their temperatures. This means that Raman spectroscopy can be used to identify what molecular species are present within a sample volume and the temperature of those species. In certain cases, the molecules may not be in thermal equilibrium. Under these circumstances, the spectral features and their relative strengths can give the nonequilibrium state of the molecule, yielding such information as the translational, rotational and vibrational temperatures. Thus, Raman spectroscopy may also be used to produce images of complex environments such as combusting gases, mixing gas streams, etc.

The Raman Spectrum is separated into two regions, one associated with scattering from purely rotational transitions, called Rotational Raman Scattering, and one associated with scattering from vibrational-rotational transitions, called Vibrational Raman Scattering. These two regions have different features. The, Vibrational Raman scattering has features associated with each molecular species clustered together at various locations in the spectrum, whereas the rotational Raman spectrum has all the Raman active species interleaved within it. In additional, since the rotational modes of a molecule have significantly lower energy than the vibrational modes, the Raman shift associated with rotational motion is rather small, on the order of a few wavenumbers. The vibrational shifts, on the other hand, are hundreds to thousands of wavenumbers. This means that the strong Rayleigh line is very close to the rotational spectrum and in most cases, obscures it. Thus, even though rotational Raman scattering is usually on the order of a factor often stronger than vibrational Raman, it is not often used for spectral analysis.

Much prior work has been done to develop various Raman devices that can effectively collect and analyze the Raman spectrum. This has been difficult because Raman scattering is exceptionally weak and occurs in the presence of strong Rayleigh scattering plus background from the sample cell walls and, in some cases, fluorescence. The typical Raman set-up consists of a light collection system which images the scattering onto a narrow slit, through which the light passes into a spectrometer, is dispersed by a grating and then passes out of a second slit onto a detector. In some cases the second slit is removed, and the detector is replaced by a camera. The scattering spectrum is spread out in space by diffraction from the grating. The grating is turned so the Raman line of interest passes through the slit onto the detector or the Raman spectrum is imaged by the camera, and the strong spectral background features are not seen by the camera or the detector. Often this arrangement does not give enough extinction to the other light components, and a second spectrometer stage must be added.

Various approaches to improving this set-up have been proposed.

Barrett, U.S. Pat. No. 3,909,132, proposed using an interference filter to transmit the rotational lines in order to measure temperature. This concept matches the approximately equal spacing of the rotational lines from one another to the regularly spaced transmission frequencies of an interferometric filter and recognizes that the progressive mismatch at higher energy may be used to determine the temperature.

Other attempts in the past include:

Stamm, U.S. Pat. No. 2,483,244, recognizes the need to provide a device of high dispersion to separate light of closely adjacent wavelengths to the maximum degree, such as found in Raman spectra. To accomplish this, the spectrometer system taught uses a Wernicke prism that includes in combination the use of a central liquid prism sandwiched between two end prisms of crown glass. The glass and prisms are symmetrically arranged and have substantially identical optical properties, with the central liquid section prism being filled with a clear ester or an acid. Various acids are disclosed in this reference.

Cary, U.S. Pat. No. 2,940,355, discloses two monochromator sections which receive monochomatic light from a source for permitting illumination of a sample over a greatly extended range relative to the use of a single monochromator, for reducing the intensity of background radiation relative to the intensity of the Raman light scattering or spectra-lines to be measured. The scattered light or Raman spectrum from the double monochromator is amplified and recorded.

Tochigi, et al., U.S. Pat. No. 4,586,819, discloses a Raman-scattered light is separated from the reflector laser beam by a filter, and the extracted Raman-scattered light is then passed through a single-monochromator for analyzing a sample. In the example given, the sample can be foreign matter of one micron or less in diameter on an integrated circuit wafer. The filters utilized, are indicated as being commercially available filters such as those that consist of dielectric-coated glass filters, that are selected for transmitting a predetermined wavelength band of light. The filters are used for separating the wavelength bands of the laser beam into spectra in shorter and longer wavelength regions. By comparing the spectra in these wavelength regions, the temperature of the sample under analysis can be exactly detected.

Webster, U.S. Pat. No. 4,684,258 teaches the reduction of interference fringes in a light beam passed through a passive cavity by including a Brewster-plate spoiler in the cavity, and oscillating it back-and-forth over an angle for causing the cavity resonances to tune in a frequency over a range that is a multiple of the period of the interference fringes. A diode laser is used to direct a beam of coherent light through a lens into a prism-like cell, from which cell the beam is directed to a Brewster-plate spoiler.

Wada, U.S. Pat. No. 5,217,306, discloses the passage of light through an optical filter located in a target region where temperature is to be measured. Pulsed laser light is passed through the optical fiber resulting in Raman-scattering. The Raman-scattering light is detected for computing the temperature of the region in which the optical fiber is located. An optical filter and a branching filter are used in the system. There is no teaching of what the optical filter consists of. The light branching filter is indicated as being made up of a diffraction grading or a thin-film optical filter such as a multilayered dielectric film.

Alfano, et al., U.S. Pat. No. 5,261,410, provides for irradiating human tissue with a beam of infrared monochromatic light, extracting the infrared Raman spectrum from the tissue, and comparing the obtained Raman spectra with standard infrared Raman spectra established as a standard for malignant tumor tissue in one case, and benign tumor tissue in another case, for making a determination as to whether the tissue under study is either benign or normal, or malignant. The system uses a fiber optic cable for transmitting laser light onto as tissue under examination, and thereafter for picking up the Raman-scattered light, and passing it through an interferometer, detector, signal processor, computer, and ratio meter for computerized comparison of the standards obtained from prior tissue studies, for thereafter displaying the results.

Maguire, U.S. Pat. No. 5,262,644, uses a fiber optic cable for irradiating a sample with coherent light from an infrared laser, and another fiber optic cable for detecting Raman-and Brillouin-scattered light for analysis.

Sai, et al., U.S. Pat. No. 5,449,233 and U.S. Pat. No. 5,618,108 describe an improvement over prior Optical Time Domain Reflectometry (OTDR) devices for measuring temperature by detecting and processing backward Raman-scattered light along points in the optical fiber. As shown in FIG. 1, the prior art system includes a light source that emits pulsed-light into a directional coupler, and therefrom into an optical filter probe used to measure temperature. The probe is arranged about an object who temperature is to be measured. The pulsed-light traveling in the fiber optic probe is Raman-scattered therein, whereby backward scattered light is returned from the fiber to the directional coupler. The Raman-backward scattered light is directed via a directional coupler into an optical filter, the latter including two filters for extracting anti-Stokes' light and Stokes' light from the backward Raman-scattered light, respectively. Filters having passbands for the wavelength of the anti-Stokes' light and the Stokes' light are used to individually extract these wavelengths of lights. As further shown, analog-to-digital filters are then use to sample and digitize the two light signals, for processing by signal processor to calculate a temperature distribution derived from the ratio of the two digitized backward Raman-scattered light signals. The improvement made in the system overcomes problems in the prior art partly by attenuating the intensity of the Stokes' light to be nearly equal to the intensity of the anti-Stokes' light. Switching means are used to select one of the two light signals, for passage through an analog-to-digital converter, and signal processing for calculating a required temperature distribution along an optical fiber.

Obremeski, et al., U.S. Pat. No. 5,498,875 discloses a system in which the analyte content of a sample is determined by passing two light signals of different wavelengths (differ by at least three nanometers) through a sample for generating two output signals. One of the output signals is a resonant signal having a wavelength independent of the associated input signal. The other output signal is a non-resonant signal that has a peak wavelength dependent upon the wavelength of the associated input light signal. The two signals are then processed for determining the difference therebetween for providing data about the analyte content of the sample. Liquid crystal filters are used in the system to provide the modulator. In one embodiment of the invention Raman-scattered light signals are processed. In another embodiment, Rayleigh scattered light signals are processed.

Carlsen, et al., U.S. Pat. No. 5,506,678 provides for transmitting a laser beam transmitted into an elongated tubular container for a gaseous substance that is to be analyzed. The gas molecules cause a portion of the light to be Raman-scattered. The tubular enclosure for the gas sample is made highly reflective to the Raman-scattered light for increasing the intensity of the Raman-scattered light outputted from an exit slit in the tubular member to collection optics. The scattered light from the collection optic is passed through a filter, a focusing lens, and therefrom to a detector for transforming the light signals into electrical signals for processing by a signal processor.

Alsmeyer, et al., U.S. Pat. No. 5,638,172, provides for irradiating both a reference material and a chemical composition with monochromatic radiation, and thereafter detecting and processing the Raman-scattered light therefrom. Comparisons are made between the Raman spectrum from the standard relative to the Raman Spectrum obtained from the chemical sample, for analyzing the composition of the chemical sample.

Sai, U.S. Pat. No. 5,639,162, teaches pulsed-monochromatic light passed through a fiber optic temperature transducer, and the back-scattered Raman light detected and processed for determining the temperature. An optical filter is used for filtering the back-scattered Raman light and separating it into the anti-Stokes' component and the Stokes' component, for further processing.

None of these efforts, taken either alone or in combination, teach or suggest all of the benefits and utility of the present invention.

OBJECTS AND SUMMARY OF THE INVENTION

A principal object of the present invention is the provision of a method and apparatus for collecting and analyzing Raman scattered light.

Another object and advantage of the present invention is the provision of an apparatus which includes an atomic vapor cell configured to spectrally disperse the light by resonant dispersion while simultaneously suppressing the Rayleigh Scattering and other background scattering through resonant absorption.

A still further object and advantage of the present invention is the provision of a method and apparatus which employs atomic resonance to both suppress the Rayleigh scattering and disperse the Raman scattering.

It is another object of the present invention to provide a vapor cell filter to allow for rotation Raman imaging.

Another object and advantage of the present invention is the provision of a method and apparatus using the strong variation in the resonant dispersion of vapor in the vicinity of an absorption feature.

A still further object and advantage of the present invention is the provision of a method and apparatus which is characterized by, at frequencies lower than the absorption feature, the refractive index increases rapidly as it approaches resonance until it reaches a maximum close to the lower frequency edge of the absorption feature.

A still further object and advantage of the present invention is the provision of a method and apparatus where, on the high frequency side of an absorption feature, the refractive index decreases rapidly as it approaches resonance until it reaches a minimum close to the upper edge of the absorption feature.

A still further object and advantage of the present invention is the provision of a device where a laser is used to illuminate a sample containing unknown molecular species.

A still further object and advantage of the present invention is the provision of a method and apparatus where a laser is tuned in the vicinity of the absorption so that the Rayleigh light from the sample is strongly attenuated.

A further object and advantage of the present invention is the provision of a method and apparatus where Raman light is spatially dispersed by an atomic vapor.

It is even an additional object of the present invention to provide an atomic vapor cell filter which bends light rays passing therethrough to spatially displace Raman light.

It is still even an additional object of the present invention to provide an atomic vapor cell filter which displaces Raman lines different amounts so the Raman spectrum can be recorded.

It is even another object of the present invention to provide an atomic vapor cell that functions as both a filter to suppress background and Rayleigh scattering, and simultaneously, as a dispersive element for imaging spectral lines.

It is still another object of the present invention to use an atomic vapor cell filter to allow for imaging of nearby molecular species.

It is still even another object of the present invention to use an atomic vapor cell to enable Raman scattering imaging of complex combustion processes such as inside engines, and of biological samples.

The Dispersive Atomic Vapor Raman Filter of the present invention takes advantage of two features of atomic resonance to both suppress the Rayleigh scattering and disperse the Raman scattering. A very narrow line width laser is used to illuminate the sample. This laser is tuned in the vicinity of the absorption feature of some atomic vapor such as mercury. The resonant dispersion of the vapor is well known to strongly vary in the vicinity of such an absorption feature. At frequencies lower than the feature, the refractive index increases rapidly until it reaches a maximum close to the lower frequency edge of the absorption feature. On the high frequency side of the feature, the refractive index behaves similarly, however in this case as the frequency approaches the resonance, the refractive index rapidly decreases until it reaches a minimum just above the absorption frequency. If the laser is tuned in the vicinity of the absorption, then the Rayleigh light is strongly attenuated. The Raman light, however is frequency shifted away from the resonance line and is therefore transmitted through the filter. If the filter is constructed so that the dispersive nature of the atomic vapor in the vicinity of the absorption line bends the light rays as they pass through the atomic vapor cell, then the Raman light can be spatially displaced. Due to the fact that the refractive index varies with frequency, each Raman line is displaced a different amount, so a Raman spectrum can be recorded.

There are several ways to construct an atomic cell so that it will disperse the light. One way is to build the cell in the form of a prism, with the entrance and exit windows both sloped toward each other. If these windows are each set at Brewster's angle with respect to the Raman light, then there will be minimum loss for one polarization of scattered light. A more sophisticated cell may be constructed of numerous such prism elements to further increase the dispersion of the light passing through. Alternatively, a cell may have a temperature profile across it so there is a density gradient. Then, the refraction of the light from the density gradient will be a function of the index of refraction and thus different Raman frequencies will be displaced different amounts.

The embodiments of the present invention include an imaging system where scattering of laser light from a sample is imaged onto a camera through the cell. If the cell is placed near the imaging lens or between two imaging lenses, then the light passing through the cell will be deflected such that each individual Raman line will form its own slightly displaced image. If the laser beam is too thick, then these images will overlap and good spectral discrimination cannot be achieved. Resolution can be improved at the expense of signal strength by initially imaging the scattering onto a narrow slit and then re-imaging the light through the atomic filter. In this case the spectral limit will be determined by the width of the slit as well as the dispersion of the filter. Other embodiments of the present invention include light collection in the forward and reverse direction. In the forward direction the full power of the laser must be removed by a combination of spatial filtering and the atomic vapor filter. In the reverse direction the laser scattering is much weaker. The advantage of imaging in the forward and reverse directions is that the apparent collection volume becomes larger, so weaker Raman signals can be measured. The reverse scattering direction is particularly useful for single probe analyses where the laser beam is delivered and the signal collected through the same optical port or optical fiber bundle.

Once the configuration is chosen, the signals associated with particular species or with particular sample characteristics can be identified. The signal may be collected with a signal detector if the laser is tuned or the detector is moved across the Raman spectrum. Otherwise, a spatial light detector such as a camera may be used. In this case, multiple lines can be simultaneously imaged, so the sample can be analyzed in a single laser shot if there are enough photons collected. Of course multiple shots give better signal to noise discrimination unless the sample is changing with time. This image can be analyzed line by line, or it can be analyzed using spatial filtering techniques to identify generic sample properties. For example, the presence of certain substances can be identified by taking an image of those species in a test cell and then looking for those features in the sample image, without resorting to a line by line analysis.

Rotational Raman cross sections of typical gases are one to two orders of magnitude larger than vibrational Raman cross sections, however, because the spacing of the rotational levels is very small (~1000 times less than the vibrational spacing), and because the manifold of rotational lines lies very near the much stronger Rayleigh line, most Raman measurements have focused on vibrational scattering. The present invention, however, provides a method and apparatus which is particularly useful for rotational Raman imaging and is characterized by strong Rayleigh line rejection, high spatial and spectral resolution and high collection efficiency.

One embodiment of the invention uses a narrow line width high power ultraviolet laser source and a mercury vapor cell. The cell is formed into a prism (with angled end windows) and is placed in front of a camera. The laser is tuned to the mercury resonance and illuminates the sample gas along a line.

BRIEF DESCRIPTION OF THE DRAWINGS

Other important objects and features of the invention will be apparent from the following Detailed Description of the invention taken in connection with the accompanying drawings in which.

DETAILED DESCRIPTION OF THE INVENTION

The apparatus of the present invention utilizes an atomic vapor cell filter that is analogous to a regular prism. The atomic vapor cell, generally indicated at 10, is shown along with the variation in the real part of the index of refraction, in FIGS. 1 and 2.

Figure 1:
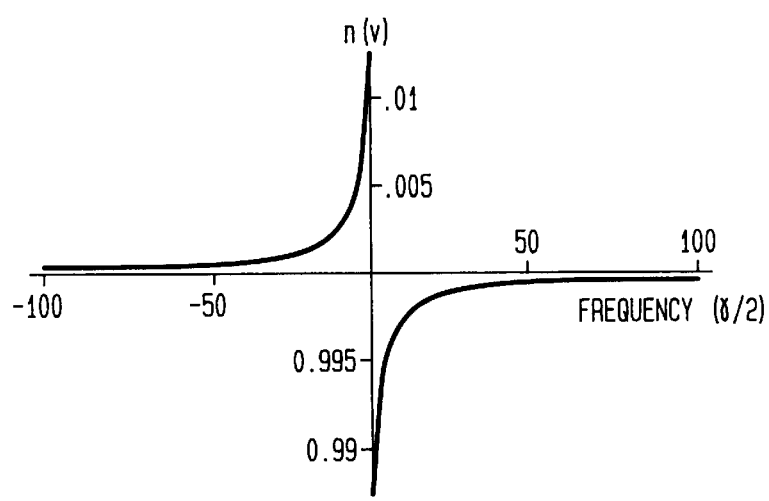
FIG. 1 is a plot of the change in index of refraction near resonance.

FIG. 1 is a plot of the change in index of refraction near resonance. The frequency axis is normalized by γ2, the linewidth of the resonant transition. The strong dependence of the index near the mercury resonance causes significant spatial dispersion for small spectral shifts (as is typical of rotational Raman lines) yielding high spectral sensitivity. The filter also provides strong absorption (modeled to be many orders of magnitude) of resonant light. The absorption is used to suppress the Rayleigh scattering which obscures the rotational lines when using conventional approaches. Spatial information is preserved along the beam, while the signal dispersed in the second dimension is a measure of the spectral content of the scattered light. Light far from resonance sees little dispersion and falls on the center line.

Figure 2:
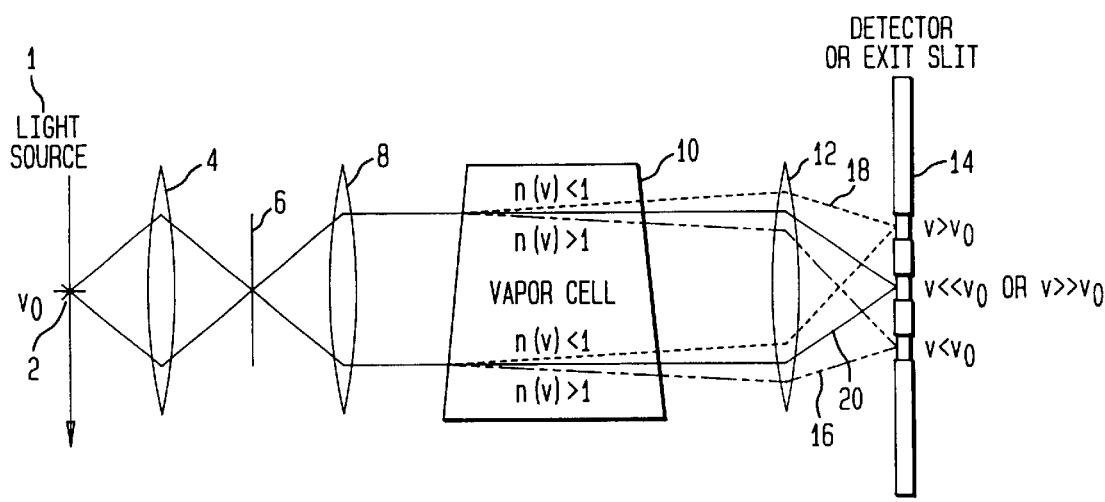
FIG. 2 is a schematic view of the apparatus of the present invention.

FIG. 2 is a schematic view of the filter of the invention. A source of light 1 is optically coupled to illuminate sample 2. The light source could be a laser such as Ti: Sapphire laser, preferably a high power, tunable, narrow linewidth, frequency-tripled Ti: Sapphire laser. High power, continuous AlGaAs diode lasers can be operated at the cesium vapor frequency, as well. Likewise, the light source could be an atomic vapor lamp which could be optically coupled to at least one narrow line width spectral filter. Light scattering from sample 2 is imaged through lens 4 to a spatial filter 6 collected by a second lens 8 and passed through a vapor prism 10, then imaged by a lens 12 onto a detector or exit slit 14. This detector or exit slit could be a match filter for identifying specific features of a sample. The output of the vapor prism 10 is represented by lines 16, 18 and 20. Light far from the vapor resonance is undeviated line 20. Light on resonance is absorbed. Light spectrally higher than resonance is shifted up, line 18 (due to an index of refraction less than one). Light at lower frequencies is shifted down, line 16.

The combination of filter 6 and vapor prism 10 creates a narrow passband spectral filter capable of frequency resolved imaging of Raman light scattering with strong spectral rejection of out-of-band Raman, Rayleigh and Mie scattering. The filter is based on the resonant effects on index of refraction, and is used to spatially separate small spectral shifts. It is capable of simultaneous 1-D measurements of multiple frequencies.

Figure 3:
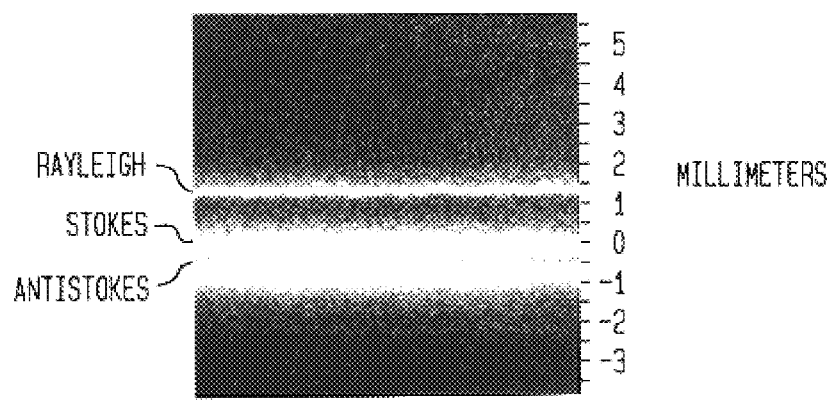
FIG. 3 is a photograph of rotational Raman scattering from CO.
Figure 4:
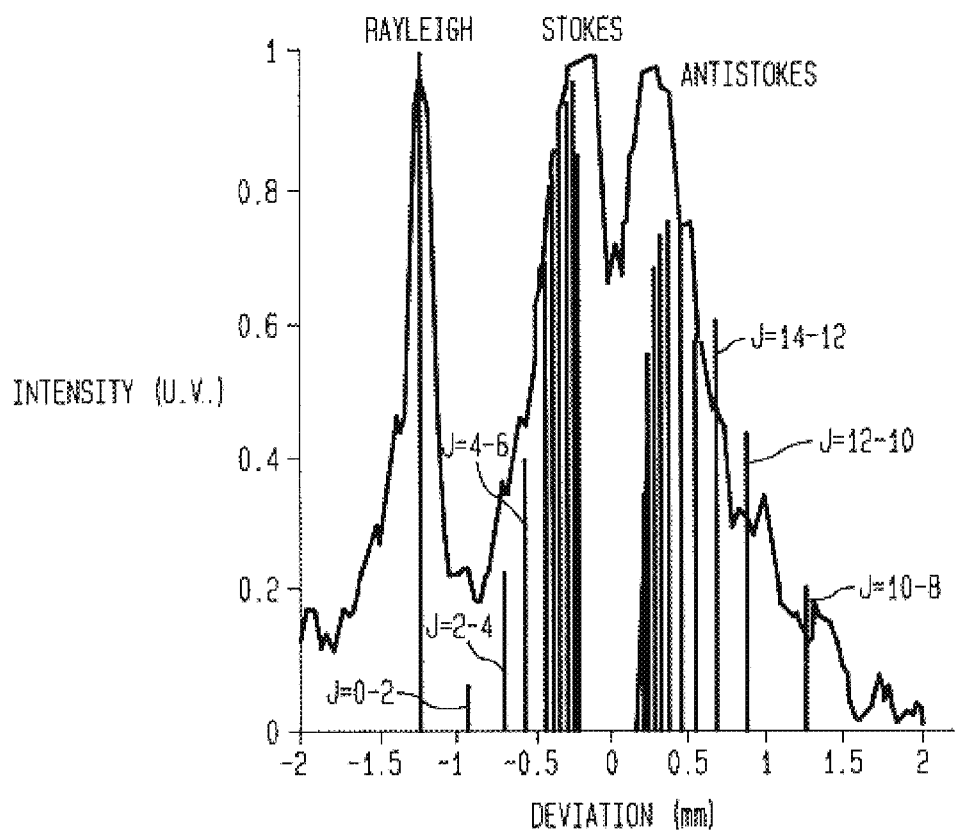
FIG. 4 is a plot of average signal level vs. spatial deviation of a portion of FIG. 3.

FIGS. 3 and 4 are images of rotational Raman scattering from $CO_2$. FIG. 3 is a fifty shot image obtained on a camera. FIG. 4 is a plot of average signal level v. spatial deviation across a twenty pixel sample region of FIG. 3. In FIG. 3, the laser was slightly detuned from the filter resonance such that the Rayleigh line is deviated left, the Stokes lines are less deviated in the same direction, while the anti-Stokes lines are deviated right. The signal strength of the Rayleigh line is reduced by several orders of magnitude, down to approximately the level of the rotational Raman signal. The Rayleigh line could be fully suppressed, but it is shown here to give a measure of the filter resolution and can be used as a simultaneous measurement of the molecular density of the sample or for laser energy calibration.

As shown in FIG. 4, the Rayleigh line as well as Stokes and Anti-Stokes bands are clearly visible. The spatial resolution of the system is not sufficient to fully resolve the individual rotational lines; however, the peaks of some of the lines (e.g. J=2–4 and J=4–6) are visible.

A model for the operation of the dispersive filter of FIG. 2 predicts Rayleigh and Raman signals. The predicted line locations and intensities are shown in FIG. 4. The profile provides a means of measuring temperature (from the Boltzmann distribution), species identification and detection (from the spatial/spectral signature), and species density (from the signal strength). The Rayleigh line gives the total molecular density in the sample. The vibrational Raman signal shows up at the detector center line and is far weaker than the rotational. For $CO_2$, the integrated rotational cross section is approximately 110 times larger than the vibrational.

Figure 5:
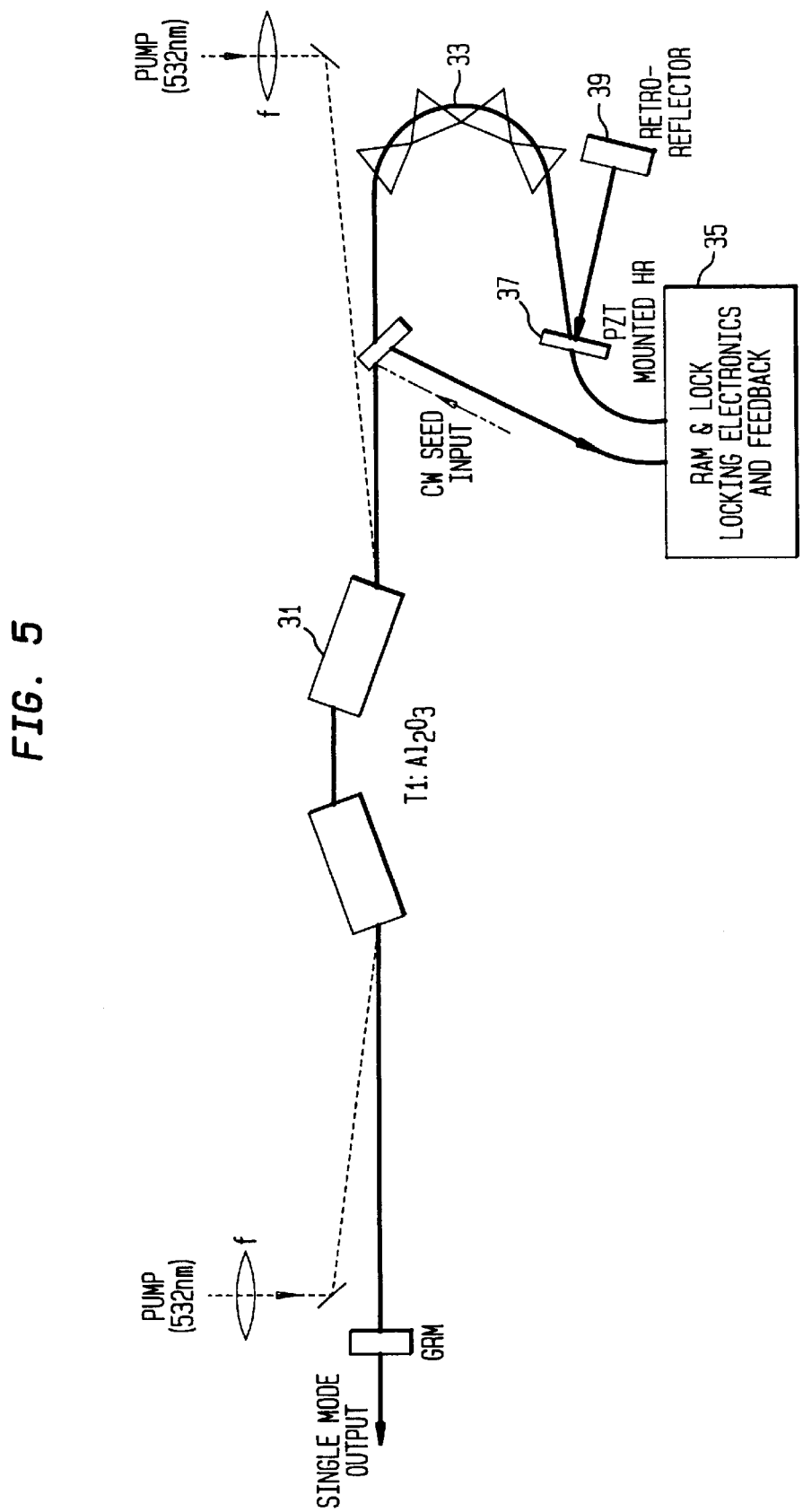
FIG. 5 is a schematic view of a pulsed laser used in the invention.

The filter is paired with an injection seeded, cavity locked, frequency tripled Ti: Sapphire laser which produces >30 milli joules/pulse of single mode, tunable light in the vicinity of 253.7 nm. As shown in FIG. 5, ultraviolet laser radiation is achieved by frequency tripling the output of an injection seeded, cavity-locked Ti: Sapphire laser. The seed source, a continuously tunable, cw Ti: Sapphire laser 31, is tuned by modifying its effective cavity length, and is stabilized via amplitude modulation feedback through an intra cavity talon. This seed laser 31 is injected into the pulsed Ti: Sapphire resonator 33 which is pumped by a frequency doubled Nd: LF. A cavity locking mechanism, Ramp and Lock 35, is employed to insure single mode output from the pulsed resonator. The Ramp and Lock 35 operates with a piezoelectric transducer (puzt) 37 mounted high reflector assembly 39 which replaces the traditional high reflector in the pulsed cavity. Before every firing of the pump laser 31, the unstable resonator 33 acquires a lock to the cw seed frequency by translating (ramping) the pzt 37 and changing the resonator cavity length. As the pulsed cavity's length is swept, a photo-diode monitors the intensity of the cw seed laser as it passes through the unstable resonator. Because the pulsed resonator acts as a low finesse etalon, fringes are observed in the cw intensity. A proportional-integral locking mechanism is used to stabilize the resonator cavity length so that a constant fringe height of the cw light intensity is observed. The lock position set point is variable, so the laser may be locked to single mode output (peak fringe height), or dual mode output (minimum peak height). This variable lock set point gives a means of empirically accounting for frequency chirp in the pulsed cavity, when the Ti: sapphire crystals are pumped. Because the pulsed resonator locks to the cw seed source before every pulse, single mode operation is maintained even if the frequency is tuned rapidly and discontinuously. This feature allows for rapid data collection, and in-band/out-of-band normalization of a filtered signal on a shot by shot basis.

A pair of non linear crystals are used for type-I doubling and subsequent type II mixing to generate the tunable ultraviolet light. When operating in a single longitudinal mode, the Ti: Sapphire achieves 265 mJ/pulse at 761 nm. The output is nearly the spectral transform limit of the 7 ns (fwhm) pulse. At 254 nm, in excess of 37 mJ/pulse of single mode tunable output is achieved. The 14% external conversion of IR to ultraviolet is limited by the mixing step. Such a laser system is useful where run time and acoustic stability are factors. The cavity locking mechanism insures rapid data collection and excellent stability.

Figure 6:
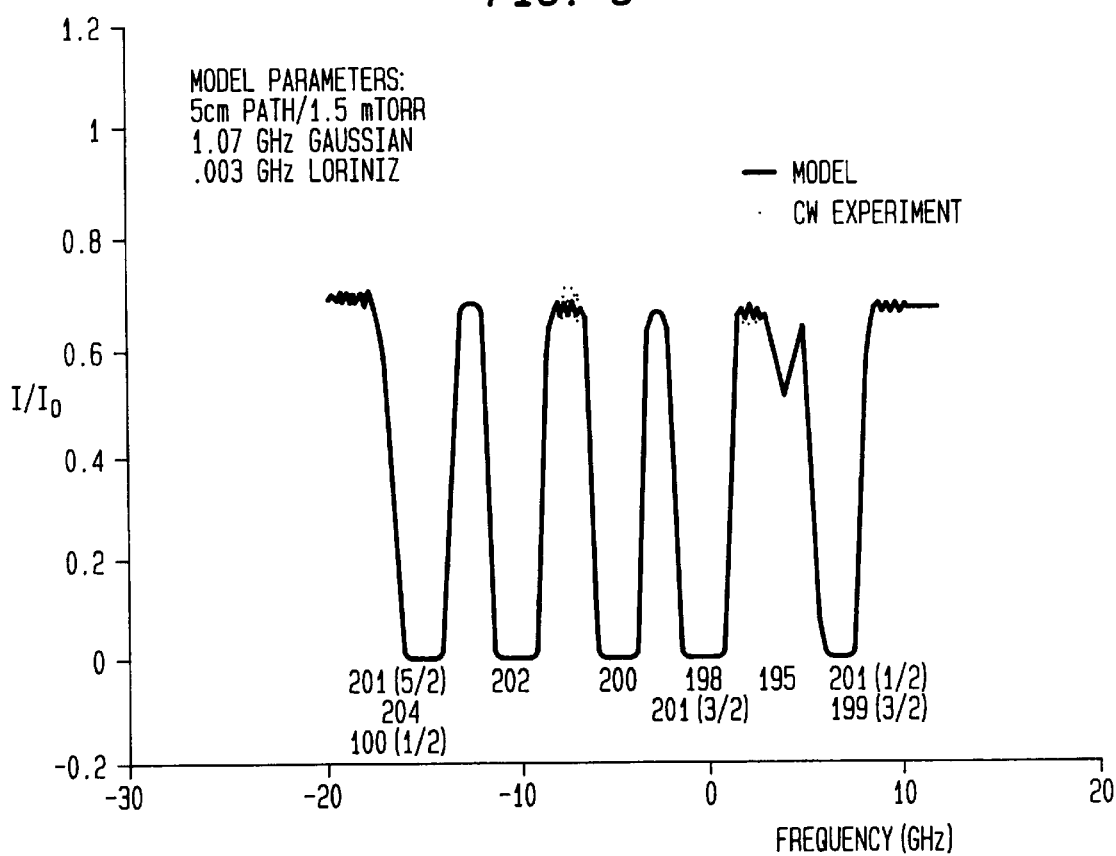
FIG. 6 is an absorption profile of the cell of FIG. 2.

Spectral filtering is achieved by exploiting the nearly ideal characteristics of atomic/molecular vapor filters. The well understood $^3P$-$^1S$ transition of atomic mercury features strong, resonant (ground state) absorption at 253.7 nm. The transmission profile of a 5 cm pathlength cell, held at 1.5 mTorr (with no buffer gas) is shown in FIG. 6. The six absorption features are due to the seven naturally occurring isotopes of mercury (listed above the transitions) and hyperfine splitting of the odd isotopes. The sharp walls give excellent spectral discrimination, of better than $1{:}10^6$, while its large oscillator strength make it an excellent absorber. On line center the mercury 202 line is modeled to attenuate approximately 25 orders of magnitude. Because mercury does not exhibit any out of band absorption, the absorption parameters may be easily manipulated by controlling the vapor pressure and temperature of the vapor cell. As a consequence, the optical depth may be increased dramatically (yielding a theoretical 10,000 orders of magnitude attenuation or more). Simultaneously, the width of the absorption band may be altered to give varying profiles as desired for a particular application.

The invention uses the dispersive properties of the mercury vapor as applied to a narrow band transmission filter. The filter takes advantage of the anomalous dispersion of the mercury vapor near resonance. Near the mercury transition the index of refraction is strongly frequency dependent, and hence can be used to create a vapor prism, mapping small spectral changes into spatial variation. The direct application of this filter is to imaging rotational Raman scattering, while simultaneously suppressing the strong elastic Mie and Rayleigh scattering. However, the invention, in other embodiments with greater dispersion, may be useful in imaging vibrational Raman scattering.

For limited light applications, such as Raman imaging, a filter based on resonance enhanced dispersion, is used. The cell is based on the well known expression for the real part of the index-or-refraction given by:

$$n^1 = 1 + \frac{e^2}{2M_e} Nf \frac{1}{\varepsilon_o} \left[ \frac{(\omega^2 - \omega_o^2)}{(\omega^2 - \omega_o^2)^2 + \gamma^2 \omega^2} \right] \quad (1)$$

where:
| | | | |
|---|---|---|---|
| e | is the electron mass | $M_e$ | is the electron mass |
| N | is the number density | f | is the oscillator strength |
| $\varepsilon_o$ | is the electric permativity | $\gamma$ | is the linewidth |
| $\omega$ | is the radial frequency | $\omega_o$ | is the resonant frequency |

Using the strong variation in index of refraction, a prism is constructed from a vapor near resonance. A controlled amount of vapor is contained between two angled windows. Incident light imaged through this cell is refracted according to its input frequency, equation (1), Snell's law. The frequency dependent refraction produces spatial deviation which may be imaged on a CCD array or camera. Small spectral shifts become significant deviations in space. Further, tuning the interrogation laser appropriately, the cell provides excellent background suppression of elastic scattering (as described earlier), while imaging and discriminating small shifts from resonance, as with rotational Raman scattering. This concept is depicted in FIG. 1, showing a plot of equation (1). For incident light at a lower frequency than the resonance, the index is greater than 1 (shown as a long dashed-line 16 in FIG. 2). As this scattered light is imaged through the vapor cell, it is deviated down (towards the input normal) on the detector. For light spectrally shifted to higher frequency (the short dashed line 18), the index is less than one, and the light is bent away from the input normal shifted up on the detector. For light far from resonance, the index of refraction is 1, and the propagation path is undeviated (solid line 20). Light on resonance is suppressed due to the absorption. The light that is deviated most significantly is that light closest to resonance, making this device particularly sensitive to small spectral shifts.

Figure 9:
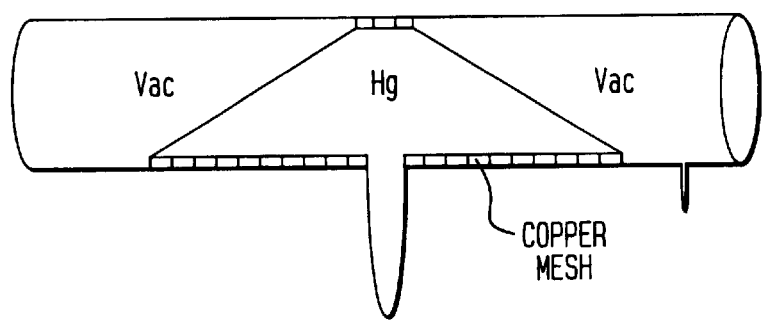
FIG. 9 is a schematic view of the filter shown in FIG. 1.

The dispersion filter, as shown in FIG. 9, consists of a pair of concentric all quartz cells, the outer of which are surrounded by a large aluminum sheath. The inner cell consists of a main body with 2" diameter clear aperture Brewster angle windows, and a side arm cold tip containing 5 gms of mercury. The main body of the inner cell is jacketed with a copper heat conductor which is used to control the temperature and prevent condensation on the Brewster windows. The combination of inner and outer cell allows heating of the inner Brewster windows while simultaneously avoiding thermal room currents which would induce additional refraction. Separate heaters and temperature controllers are used to insure that the inner cell body is held at a constant temperature which is slightly warmer than the sidearm cold tip (which controls the vapor pressure). Operating conditions for these experiments were roughly 190° C. for the inner cell body temperature and 170° C. for the side arm. This corresponds to a mercury vapor pressure of 6.3 torr and a thermally broadened absorption linewidth of 1.2 Ghz. It is significant to point out that the line center attenuation for this cell is predicted to be in excess of $10^4$/cm, due to the exceedingly high value of the imaginary (or absorptive) part of the index-of-refraction. The cell, therefore, simultaneously achieves high suppression on line center and high dispersion off line center. This can be important for imaging applications in the presence of significant elastic scattering.

Figure 7:
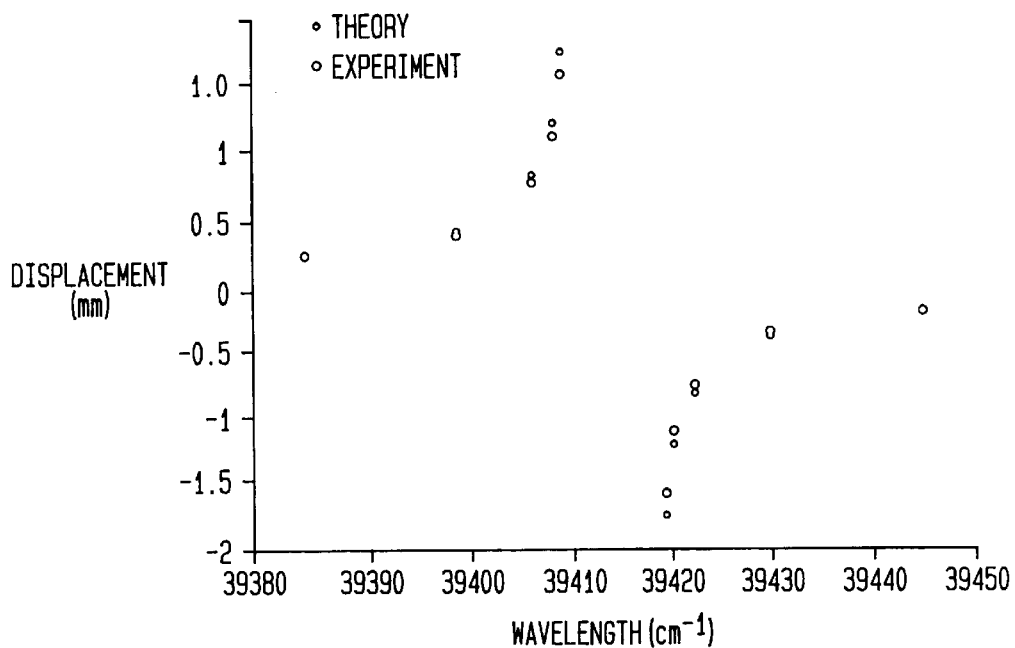
FIG. 7 is plot of vapor dispersion of the cell of FIG. 2.

In order to provide an experimental verification of the predicted dispersion, a target was illuminated with the third harmonic output of the Ti: Sapphire laser and the scattering collimated with an f/10 lens through the vapor prism. A slit was paced near the scattering source and the refracted beam reimaged onto a microchannel plate intensified video camera. As the laser was tuned in wavelength a camera recorded the displaced image of the slit as a function of detuning from line center of the mercury vapor resonance. The results are illustrated in FIG. 7, along with the prediction from equation (1). The agreement is to within the combined uncertainty in the imaging system calibration and the cell pressure.

Figure 8:
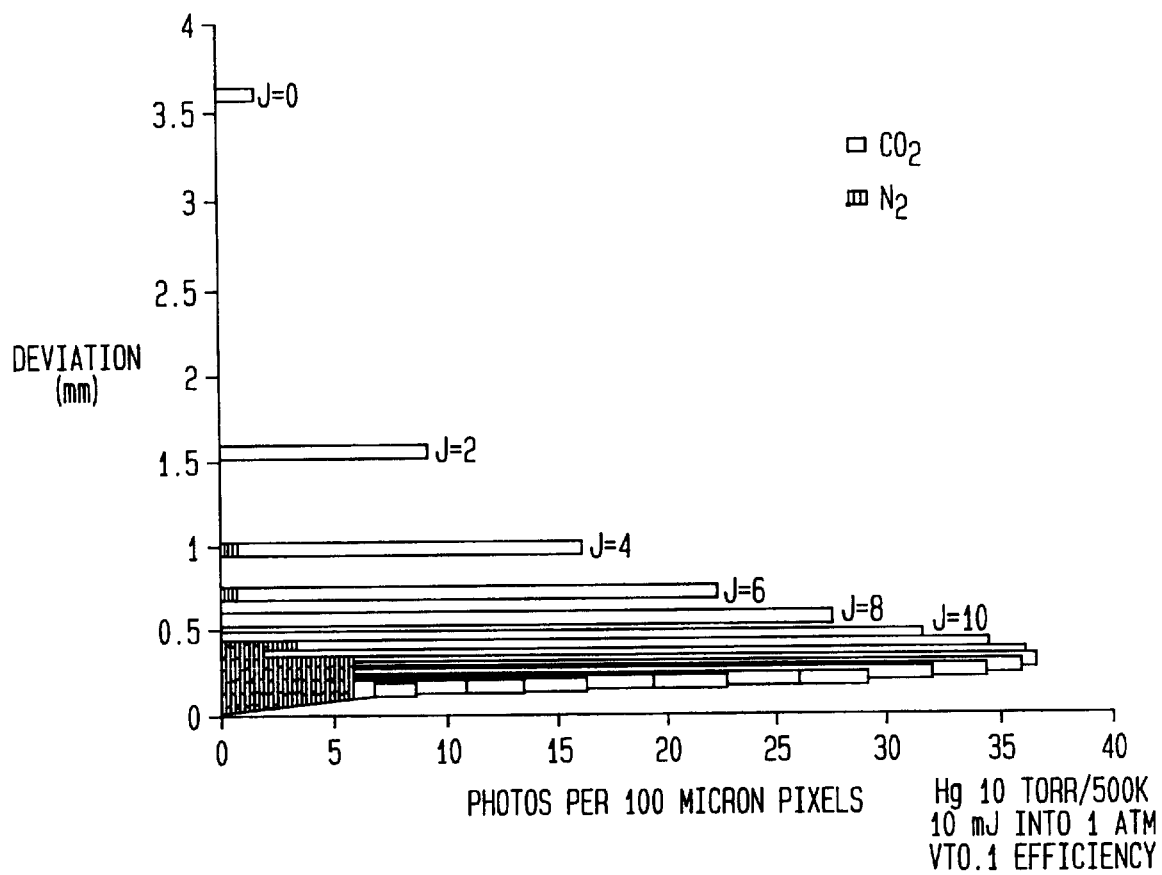
FIG. 8 is a plot of deviation and signal levels of $CO_2$ and $N_2$ of the cell of FIG. 7.

Applying this model gives predictions for imaging rotational Raman scattering from various species. FIG. 8 gives model predictions for the spatial deviation, and signal strength in a 100 micron pixel resolution element. The modeled laser intensity is 10 mJ/pulse; the cell vapor pressure is 10 torr;

collection if f/20, with a 1 meter imaging length. Plotted are the predicted Stokes shifted rotational Raman scattering lines for $CO_2$ and $N_2$ at STP. As observed, the different spectral signatures of the two species become different spatial signatures.

A variety of mechanisms may be used to increase the dispersion, and hence sensitivity of this filter. Because the filter relies upon the index variation at the Brewster window interface, and not the path length through the vapor, a multi-pass or series of vapor prisms additively improve the dispersion. Notably, the dispersion increases with increasing angle of incidence, according to Snell's Law. Unfortunately as the incidence angle exceeds Brewster's angle, the reflection loss at the input window becomes significant. A means of producing a large effective incidence angle without reflection loss is to create a density gradient in the mercury vapor which is perpendicular to the input radiation (i.e. a vertical gradient in the cells shown in FIG. 2). In essence the gradient in number density (which may be made quite dramatic with temperature variation), produces a very large effective incidence angle. Meanwhile the input window may be placed at any angle, including Brewster's angle to reduce reflection loss.

The refractive filter of the present invention provides superior performance in a frequency interval near to the filter resonance compared to conventional grating spectrometers. Significantly larger signal to noise may be obtained via rotational Raman scattering rather than vibrational Raman in many cases.

The resonant dispersion Raman spectrometer of the present invention has applications, inter alia, as a diagnostic for determining molecules comprising a sample volume. Such a device can be used in medical diagnostics for determining molecular constituents of blood or of a tumor. Such analysis could be "on-line" in real time and/or in-situ. Such a device could effectively look through skin for diagnosing cancer or other pathology. Additional applications of the present invention include monitoring pollution. As such, a device according to the present invention could be interconnected with an engine to take readings on exhaust. Other applications of devices of the present invention are considered within the scope of the present invention.

Having thus described the invention in detail, it is to be understood that the foregoing description is not intended to limit the spirit and scope thereof. What is desired to be protected by Letters Patent is set forth in the appended claims.

What is claimed is:

1. An apparatus for dispersing Raman light scattering comprising:

an atomic vapor;

cell means for housing said atomic vapor therein; and said cell means being configured so that the Raman spectrum of light passing through said cell is dispersed by the variation of the index of refraction of said atomic vapor in the vicinity of the atomic resonance absorption line of said atomic vapor.

2. The apparatus of claim 1 wherein said cell means includes window means for changing the refraction angle of light passing through said window means, into and out of said cell means, to spectrally disperse Raman light.

3. The apparatus of claim 2 wherein said window means incudes window facets internal to said cell means for increasing the dispersion of said cell means.

4. The apparatus of claim 1 wherein said cell means has a density gradient thereacross for spectrally dispersing said Raman light.

5. The apparatus of claim 4 wherein the density gradient is created in the cell by applying a temperature gradient to the cell.

6. The apparatus of claim 1 wherein said atomic vapor is characterized by absorption which suppresses Rayleigh scattered light.

7. The apparatus of claim 1 wherein said atomic vapor is characterized by absorption which suppresses background scattered light.

8. An apparatus for Raman spectroscopy comprising:

narrow line width light source means tuned substantially near the resonance of an atomic vapor for illuminating a sample;

light collection means for collecting light scattered from said sample;

atomic vapor cell means optically coupled to said light collection means for dispersing said collected light; and detector means optically coupled to said atomic vapor cell means for detecting a portion of said dispersed light.

9. The apparatus of claim 7 wherein said narrow line width light source means comprises a laser.

10. The apparatus of claim 7 wherein said narrow line width light source comprises a narrow line width atomic resonance lamp.

11. The apparatus of claim 7 wherein said narrow line width light source means comprises an atomic vapor lamp optically coupled to at least one narrow line width spectral filter.

12. The apparatus of claim 7 further including slit or small aperture means optically coupled between said light collection means and said atomic vapor cell means through which Raman scattering is passed prior to entering said atomic vapor cell to increase the resolution of said apparatus.

13. The apparatus of claim 7 wherein said detector means comprises an array of detector elements for simultaneously detecting a portion or all of said Raman scattering and/or said Rayleigh scattering spectrums.

14. The apparatus of claim 7 wherein the detector means comprises a two dimensional array of detector elements for recording dispersed Raman and/or Rayleigh spectrum in one direction and a spatial component of the sample volume in the orthogonal direction.

15. The apparatus of claim 13 further comprising means coupled to said detector means for analyzing said Raman scattering and/or said Rayleigh scattering by pattern recognition to identify specific features of said sample.

16. A method of Raman spectroscopy comprising the steps of:

using an atomic vapor as both a filter to suppress background and Rayleigh scattering and, simultaneously, as a dispersive element for imaging separate spectral lines, whereby the highest dispersion falls closest to the resonant absorption of the filter; and tuning a light source to the resonance of the filter for suppressing Rayleigh scattering so that the lowest-lying Raman transitions see the greatest dispersion, whereby Raman imaging may be employed.

17. A method of Raman spectroscopy comprising the steps of:

tuning a narrow line width light source substantially near the resonance of an atomic vapor;

illuminating a sample with the output of said narrow line width light source;

collecting light scattered from said sample;

dispersing said collected light using an atomic vapor; and detecting a portion of said dispersed light.

18. The method of claim 17 wherein said narrow line width light source comprises a laser.

19. The method of claim 17, wherein said narrow line width light source comprises a narrow line width atomic resonance lamp.

20. The method of claim 17 wherein said narrow line width light source comprises an atomic vapor lamp optically coupled to at least one narrow line width spectral filter.

21. The method of claim 17 wherein said collected light is dispersed with an atomic vapor filter.

22. The method of claim 17 wherein said collected light is dispersed with a plurality of atomic vapor filters.

23. The method of claim 17 further comprising the step of creating a density gradient across the atomic vapor.

24. The method of claim 17 further comprising the step of housing the atomic vapor in a cell.

25. A method of using an atomic vapor cell to disperse scattered light comprising the steps of:

tuning a light source to an atomic vapor;

directing the light source at a sample;

sending scattered light to cell housing the atomic vapor;

dispersing the scattered light; and detecting the scattered light.

26. An atomic vapor cell for a Raman spectrometer comprising:

a pair of quartz cells;

an aluminum sheath surrounding the quartz cells;

an inner cell having clear aperture Brewster angle windows; and a heat conductor jacketing the inner cell.

27. The vapor cell of claim 26 wherein the inner cell further comprises a side arm cold tip.

28. The vapor cell of claim 27 wherein the side arm cold tip contains mercury.

29. The vapor cell of claim 26 further comprising temperature controllers to retain the inner cell at a constant temperature.

* * * * *